(12) United States Patent
Acharte et al.

(10) Patent No.: US 12,106,854 B2
(45) Date of Patent: Oct. 1, 2024

(54) SYSTEMS AND METHODS FOR PROVIDING VIRTUAL HEALTH SERVICES

(71) Applicant: Orchid Exchange Inc., Wilmington, DE (US)

(72) Inventors: Christian Acharte, Philadelphia, PA (US); Joseph Pomianowski, Philadelphia, PA (US); Dániel Varga, Amsterdam (NL)

(73) Assignee: Orchid Exchange Inc., Wilmington, DE (US)

( * ) Notice: Subject to any disclaimer, the term of this patent is extended or adjusted under 35 U.S.C. 154(b) by 71 days.

(21) Appl. No.: 17/839,825

(22) Filed: Jun. 14, 2022

(65) Prior Publication Data

US 2022/0310256 A1    Sep. 29, 2022

Related U.S. Application Data

(63) Continuation of application No. 17/207,024, filed on Mar. 19, 2021, now Pat. No. 11,404,164.

(60) Provisional application No. 63/153,526, filed on Feb. 25, 2021, provisional application No. 63/153,030, filed on Feb. 24, 2021, provisional application No. 63/135,152, filed on Jan. 8, 2021, provisional application No. 63/125,559, filed on Dec. 15, 2020.

(51) Int. Cl.
| | |
|---|---|
| *G16H 40/67* | (2018.01) |
| *G06Q 20/10* | (2012.01) |
| *G16H 10/60* | (2018.01) |
| *G16H 40/20* | (2018.01) |
| *G16H 80/00* | (2018.01) |

(52) U.S. Cl.
CPC .......... *G16H 40/67* (2018.01); *G06Q 20/102* (2013.01); *G16H 10/60* (2018.01); *G16H 40/20* (2018.01); *G16H 80/00* (2018.01)

(58) Field of Classification Search
CPC ........ G16H 40/67; G16H 40/20; G16H 10/60; G16H 80/00; G06Q 20/102
USPC ......................................................... 705/2–3
See application file for complete search history.

(56) References Cited

U.S. PATENT DOCUMENTS

| | | | |
|---|---|---|---|
| 6,283,761 B1 * | 9/2001 | Joao ...................... | G16H 40/67 128/923 |
| 6,988,075 B1 * | 1/2006 | Hacker .................. | G16H 10/60 705/2 |

(Continued)

*Primary Examiner* — Michael Tomaszewski
(74) *Attorney, Agent, or Firm* — Jonathan M. Waldman

(57) ABSTRACT

A virtual health system is provided that creates a digital platform to connect patients to healthcare providers. Healthcare providers create profiles that describe their healthcare specialty and provide scheduling information that indicates their availability along with preferences such as appointment or meeting length, minimum break between appointment, and price. Patients create profiles that includes demographic information as well as medical records. The patients may use the system to search for available healthcare providers using a variety of criteria, and to schedule virtual health services such as video chats. The system facilitates payment for the healthcare services, and records any notes, assignments, or prescriptions generated by the healthcare provider during the services. In the event that a patient would like to engage a different healthcare provider associated with the system, the system only allows access to the patient records after receiving permission from the patient.

16 Claims, 6 Drawing Sheets

(56) References Cited

U.S. PATENT DOCUMENTS

| | | | | |
|---|---|---|---|---|
| 7,337,123 B2* | 2/2008 | Dvorak | G16H 40/20 | 709/204 |
| 7,725,332 B1* | 5/2010 | Soong | G16H 10/60 | 600/300 |
| 8,788,284 B2* | 7/2014 | Smith | G16H 10/60 | 705/3 |
| 8,949,137 B2* | 2/2015 | Crapo | G16H 40/20 | 705/3 |
| 11,404,164 B2* | 8/2022 | Pomianowski | G16H 40/67 | |
| 2001/0051879 A1* | 12/2001 | Johnson | H04L 63/102 | 707/999.001 |
| 2001/0053986 A1* | 12/2001 | Dick | G16H 15/00 | 705/3 |
| 2002/0007284 A1* | 1/2002 | Schurenberg | H04L 69/329 | 705/2 |
| 2002/0138306 A1* | 9/2002 | Sabovich | G16H 10/60 | 705/3 |
| 2003/0050803 A1* | 3/2003 | Marchosky | G16H 10/60 | 705/3 |
| 2003/0088441 A1* | 5/2003 | McNerney | G16H 40/67 | 705/3 |
| 2004/0117215 A1* | 6/2004 | Marchosky | G16H 10/60 | 705/3 |
| 2005/0159986 A1* | 7/2005 | Breeland | G06Q 30/06 | 703/11 |
| 2005/0165627 A1* | 7/2005 | Fotsch | G16H 10/60 | 707/999.009 |
| 2005/0182661 A1* | 8/2005 | Allard | G06F 21/6245 | 705/3 |
| 2006/0229911 A1* | 10/2006 | Gropper | G16H 10/60 | 705/2 |
| 2007/0150315 A1* | 6/2007 | Bennett | G16H 10/60 | 707/999.009 |
| 2007/0294114 A1* | 12/2007 | Urali | G16H 40/67 | 705/3 |
| 2008/0133269 A1* | 6/2008 | Ching | G06Q 10/10 | 705/2 |
| 2009/0063188 A1* | 3/2009 | Schoenberg | G16H 10/60 | 705/2 |
| 2009/0099921 A1* | 4/2009 | Klein | G06Q 30/02 | 705/14.69 |
| 2009/0138281 A1* | 5/2009 | Hacker | G06Q 10/10 | 705/3 |
| 2009/0138283 A1* | 5/2009 | Brown | G06Q 10/1095 | 705/7.19 |
| 2009/0326982 A1* | 12/2009 | Deobhakta | G16H 10/60 | 705/3 |
| 2009/0327297 A1* | 12/2009 | Deobhakta | G16H 10/60 | 715/764 |
| 2010/0205005 A1* | 8/2010 | Pritchett | G16H 10/60 | 705/7.19 |
| 2010/0269157 A1* | 10/2010 | Experton | G06F 21/6245 | 726/28 |
| 2010/0305973 A1* | 12/2010 | McLaren | G16Z 99/00 | 705/3 |
| 2011/0166883 A1* | 7/2011 | Palmer | G06Q 10/10 | 705/2 |
| 2011/0313792 A1* | 12/2011 | Mault | G16H 10/20 | 705/3 |
| 2012/0143624 A1* | 6/2012 | Jena | G16H 80/00 | 705/3 |
| 2012/0303386 A1* | 11/2012 | Zavaleta | G16H 40/67 | 705/3 |
| 2013/0124226 A1* | 5/2013 | Gedala | G16H 10/60 | 705/3 |
| 2013/0173287 A1* | 7/2013 | Cashman | H04N 7/141 | 705/2 |
| 2013/0304510 A1* | 11/2013 | Chen | G16H 10/60 | 705/3 |
| 2013/0325490 A1* | 12/2013 | Abrahams | G16H 40/20 | 705/2 |
| 2014/0056417 A1* | 2/2014 | Wildman | G16H 40/20 | 379/67.1 |
| 2014/0067418 A1* | 3/2014 | Hyzy | G16Z 99/00 | 705/3 |
| 2014/0136236 A1* | 5/2014 | Lee | G16H 10/60 | 705/3 |
| 2014/0136239 A1* | 5/2014 | Miller | G16H 40/63 | 705/3 |
| 2014/0180715 A1* | 6/2014 | Phillips | G06Q 10/103 | 705/2 |
| 2014/0236612 A1* | 8/2014 | Liberty | G16H 20/10 | 705/2 |
| 2014/0236635 A1* | 8/2014 | Liberty | G16H 10/60 | 705/3 |
| 2014/0316808 A1* | 10/2014 | Romatoski | G16H 30/40 | 705/3 |
| 2015/0149209 A1* | 5/2015 | Raizada | G16H 10/60 | 705/3 |
| 2015/0227692 A1* | 8/2015 | Ahmed | G16H 10/60 | 705/3 |
| 2015/0234984 A1* | 8/2015 | Singer | H04L 63/0272 | 705/3 |
| 2015/0242583 A1* | 8/2015 | Edson | G16H 80/00 | 705/3 |
| 2015/0278453 A1* | 10/2015 | Joao | G16H 80/00 | 705/3 |
| 2015/0324525 A1* | 11/2015 | Saffran | G16H 10/60 | 705/3 |
| 2015/0350148 A1* | 12/2015 | Kenney | H04L 51/224 | 709/206 |
| 2016/0042483 A1* | 2/2016 | Vo | G16H 10/60 | 705/3 |
| 2016/0196408 A1* | 7/2016 | Bessette | G06Q 10/00 | 705/3 |
| 2017/0286702 A1* | 10/2017 | Cheung | H04L 63/0853 | |
| 2020/0051677 A1* | 2/2020 | Harrison | G06F 3/0483 | |
| 2020/0279658 A1* | 9/2020 | Rao | H04L 51/046 | |
| 2021/0055897 A1* | 2/2021 | Tomihisa | H04L 51/10 | |
| 2022/0189625 A1* | 6/2022 | Pomianowski | G16H 80/00 | |
| 2022/0310257 A1* | 9/2022 | Acharte | G16H 40/20 | |
| 2022/0319695 A1* | 10/2022 | Pomianowski | G16H 80/00 | |

* cited by examiner

SYSTEMS AND METHODS FOR PROVIDING VIRTUAL HEALTH SERVICES

CROSS-REFERENCE TO RELATED APPLICATIONS

The present application claims priority to U.S. Provisional Patent Application Ser. No. 63/125,559, filed on Dec. 15, 2020 and entitled "CLINICAL SCHEDULER SYSTEMS AND METHODS." The present application claims priority to U.S. Provisional Patent Application Ser. No. 63/135,152, filed on Jan. 8, 2021 and entitled "SYSTEMS AND METHODS FOR ORGANIZING GROUP MEETINGS ONLINE." The present application claims priority to U.S. Provisional Patent Application Ser. No. 63/153,030, filed on Feb. 24, 2021 and entitled "SYSTEMS AND METHODS FOR MANAGING COMMUNICATION OF HEALTHCARE INFORMATION BETWEEN HEALTHCARE PROVIDERS AND PATIENTS." The present application claims priority to U.S. Provisional Patent Application Ser. No. 63/153,526, filed on Feb. 25, 2021 and entitled "VIRTUALIZATION OF THE CLINICAL EXPERIENCE THROUGH A SEAMLESS AND INTEGRATED ONLINE HEALTHCARE PLATFORM." The present application claims priority to U.S. patent application Ser. No. 17/207,024, filed on Mar. 19, 2021 and entitled "SYSTEMS AND METHODS FOR PROVIDING VIRTUAL HEALTH SERVICES." All of these disclosures are hereby incorporated by reference in their entireties.

BACKGROUND

There are currently many problems with how mental health services are provided. First, mental health services can be expensive which may discourage patients from seeking out mental health professionals for help. Second, the availability of mental health professionals may be limited to typical business hours which may make scheduling an appointment difficult for individuals with busy or non-standard schedules. Third, in the age of COVID, some potential patients may be unwilling or reluctant to travel or meet in-person with a mental health professional.

It is with respect to these and other considerations that the various aspects and embodiments of the present disclosure are presented.

SUMMARY

In one embodiment, a virtual health system is provided that creates a digital platform to connect patients to healthcare providers. Healthcare providers create profiles that describe their healthcare specialty (or specialties) and provide scheduling information that indicates their availability along with preferences such as appointment or meeting length, minimum break between appointment, and price, for example. Patients create profiles that include demographic information as well as medical records. The patients may use the virtual health system to search for available healthcare providers using a variety of criteria, and to schedule virtual health services such as video chats. The virtual health system facilitates payment for the healthcare services, and records any notes, assignments, or prescriptions generated by the healthcare provider during the virtual health services. In the event that a patient would like to engage with another healthcare provider associated with the virtual health system, the system only allows access to the patient records after receiving explicit permission from the patient.

In an embodiment, a method for providing virtual healthcare services is provided. The method includes: providing a graphical user interface by a computing device; receiving, through the graphical user interface, a schedule associated with a first healthcare provider by the computing device, wherein the schedule includes the availability of the first healthcare provider over a first duration of time; receiving, through the graphical user interface, an appointment length for the first healthcare provider by the computing device; receiving, through the graphical user interface, a break length for the first healthcare provider by the computing device; receiving, through the graphical user interface, an alignment for the first healthcare provider by the computing device; receiving, through the graphical user interface, a request for a virtual healthcare service with the first healthcare provider from a patient by the computing device, wherein the request includes a second duration of time, and wherein the second duration of time is within the first duration of time; based on the schedule, the appointment length, the break length, and the alignment, determining a plurality of time periods during the second duration of time when the first healthcare provider is available to conduct the virtual healthcare service by the computing device; and presenting, through the graphical user interface, some or all of the determined plurality of time periods to the patient by the computing device.

Embodiments may include some or all of the following features. The method may include receiving, through the graphical user interface, a selection of one of the presented plurality of time periods; and in response to the selection, modifying the schedule associated with the first healthcare provider. The method may include automatically providing the first healthcare provider access to medical records associated with the patient in response to the patient selecting one of the presented plurality of time periods. The method may include: determining that a current time is the selected time period; and in response to the determination that the current time is the selected time period, initiating the virtual healthcare service between the patient and the first healthcare provider. Initiating the virtual healthcare service may include establishing a video conference between the patient and the first healthcare provider, or an audio conference between the patient and the first healthcare provider. The method may include: determining that the virtual healthcare service has started; and in response to the determination that the virtual healthcare service has started: debiting an amount from the patient for the virtual healthcare service; and crediting the amount to the first healthcare provider minus a service fee. The method may include: determining that the patient has canceled the virtual healthcare service; and in response to the determination that the patient has canceled the virtual healthcare service: debiting a cancelation fee from the patient for the virtual healthcare service; and crediting the cancelation fee to the first healthcare provider minus a service fee. The method may include: receiving a request to access medical records associated with the patient from the first healthcare provider; in response to the request, requesting permission from the patient to allow the first healthcare provider access to the medical records; receiving permission from the patient to allow the first healthcare provider access to the medical records; and in response to receiving the permission, providing the first healthcare provider access to the medical records. The method may include: receiving a referral for patient to a second health provider from the first health provider; in response to the referral, requesting permission from the patient to allow the second healthcare provider access to the medical records;

receiving permission from the patient to allow the second healthcare provider access to the medical records; and in response to receiving the permission, providing the second healthcare provider access to the medical records.

In an embodiment, a method for providing virtual healthcare services is provided. The method includes: maintaining medical records for a patient associated with a first healthcare provider by a computing device; providing access to the medical records to the first healthcare provider by the computing device; receiving a request from the first healthcare provider to provide access to the medical records to a second healthcare provider by the computing device; in response to receiving the request from the first healthcare provider, requesting permission from the patient to allow the second healthcare provider access to the medical records by computing device; receiving permission from the patient to allow the second healthcare provider access to the medical records by the computing device; and in response to receiving the permission, providing the second healthcare provider access to the medical records by the computing device.

Embodiments may include some or all of the following features. The method may include: receiving a schedule associated with the second healthcare provider, wherein the schedule includes the availability of the second healthcare provider over a first duration of time; receiving an appointment length for the second healthcare provider; receiving a break length for the second healthcare provider; receiving an alignment for the second healthcare provider; receiving a request for a virtual healthcare service with the second healthcare provider from a patient, wherein the request includes a second duration of time, and wherein the second duration of time is within the first duration of time; based on the schedule, the appointment length, the break length, and the alignment, determining a plurality of time periods during the second duration of time when the second healthcare provider is available to conduct the virtual healthcare service; and presenting some or all of the determined plurality of time periods to the patient. The method may further include: receiving a selection of one of the presented plurality of time periods; and in response to the selection, modifying the schedule associated with the second healthcare provider. The method may further include: determining that a current time is the selected time period; and in response to the determination that the current time is the selected time period, initiating the virtual healthcare service between the patient and the second healthcare provider. Initiating the virtual healthcare service may include establishing a video conference between the patient and the second healthcare provider, or an audio conference between the patient and the second healthcare provider. The method may include: determining that the virtual healthcare service has started; and in response to the determination that the virtual healthcare service has started: debiting an amount from the patient for the virtual healthcare service; and crediting the amount to the second healthcare provider minus a service fee. The method may include: determining that the patient has canceled the virtual healthcare service; and in response to the determination that the patient has canceled the virtual healthcare service: debiting a cancelation fee from the patient for the virtual healthcare service; and crediting the cancelation fee to the second healthcare provider minus a service fee.

In an embodiment, a system for providing virtual healthcare services is provided. The system includes at least one computing device and a memory storing instructions. The instructions when executed by the at least one computing device cause the at least one computing device to: provide a graphical user interface; receive, through the graphical user interface, a schedule associated with a first healthcare provider by the computing device, wherein the schedule includes the availability of the first healthcare provider over a first duration of time; receive, through the graphical user interface, an appointment length for the first healthcare provider; receive, through the graphical user interface, a break length for the first healthcare provider; receive, through the graphical user interface, an alignment for the first healthcare provider; receive, through the graphical user interface, a request for a virtual healthcare service with the first healthcare provider from a patient, wherein the request includes a second duration of time, and wherein the second duration of time is within the first duration of time; based on the schedule, the appointment length, the break length, and the alignment, determine a plurality of time periods during the second duration of time when the first healthcare provider is available to conduct the virtual healthcare service; and present, through the graphical user interface, some or all of the determined plurality of time periods to the patient.

Embodiments may include some or all of the following features. The instructions when executed by the at least one computing device may cause the at least one computing device to: receive and display messages between the first healthcare provider and a second healthcare provider by the graphical user interface; determine that at least some of the messages are related to the patient; and in response to the determination, associate the at least some of the messages with electronic medical records associated with the patient. The instructions when executed by the at least one computing device may cause the at least one computing device to: receive and display messages between the first healthcare provider and a second healthcare provider by the graphical user interface; receive a selection of a subset of the displayed messages, wherein the displayed messages in the subset pertain to the patient; and associate the subset of the displayed messages with electronic medical records associated with the patient.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there is shown in the drawings example constructions of the embodiments; however, the embodiments are not limited to the specific methods and instrumentalities disclosed. In the drawings.

DETAILED DESCRIPTION

Figure 1:
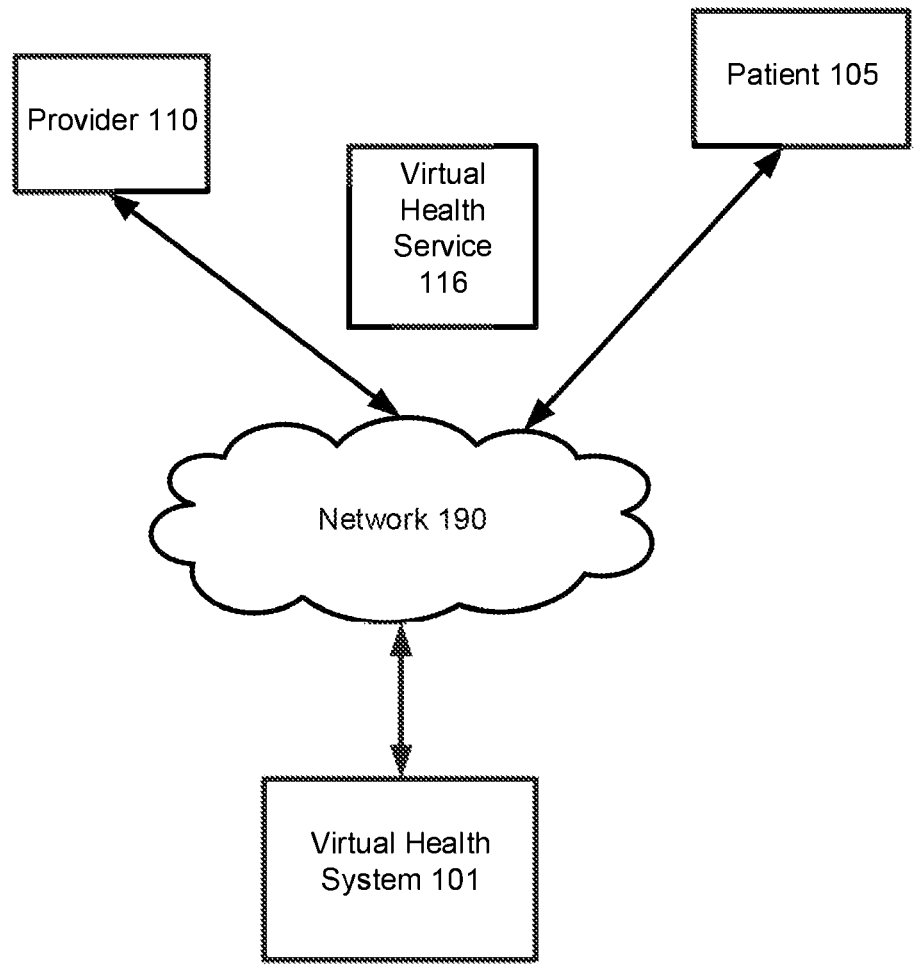
FIG. 1 is an example environment for providing virtual health services to a patient by a provider.

This description provides examples not intended to limit the scope of the appended claims. The figures generally indicate the features of the examples, where it is understood and appreciated that like reference numerals are used to refer to like elements. Reference in the specification to "one embodiment" or "an embodiment" or "an example embodiment" means that a particular feature, structure, or characteristic described is included in at least one embodiment described herein and does not imply that the feature, structure, or characteristic is present in all embodiments described herein.

FIG. 1 is an example environment 100 for providing virtual health services 116 to a patient 105 by a provider 110. As shown, the environment 100 includes a provider 110, a patient 105, and a virtual health system 101 communicating through a network 190. While only one provider 110 and one patient 105 are shown, it is contemplated that there may be multiple providers 110 and/or patients 105 in the environment 100.

The provider 110 as used herein may include any provider of healthcare and medical services including mental health services. The provider 110 may include solo practitioners as well as group practices that include multiple practitioners. Providers 110 may include wellness providers, therapists, psychologists, psychiatrists, or some combination of all. Patients 105 may be any individual that receives medical or healthcare services from a provider 110.

As described above, due to many factors such as cost, time, and COVID-19, many individuals do not receive necessary health services and particularly mental health services. Accordingly, to reduce the costs and increase the availability and convenience of health services, the environment 100 may further include a virtual health system 101. The virtual health system 101 may allow patients 105 to connect with providers 110 and may facilitate the delivery of virtual health services 116 from the providers 110 to the patients 105.

As used herein, a virtual health service 116 is a health service that is provided by a provider 110 to a patient 105 remotely through a communication medium such as the internet (e.g., the network 190). Example communication mediums include video calling or video conferencing, text or chat applications (e.g., text messaging or SMS), and voice communication (e.g., cell phone, VOIP, and traditional telephony).

Figure 2:
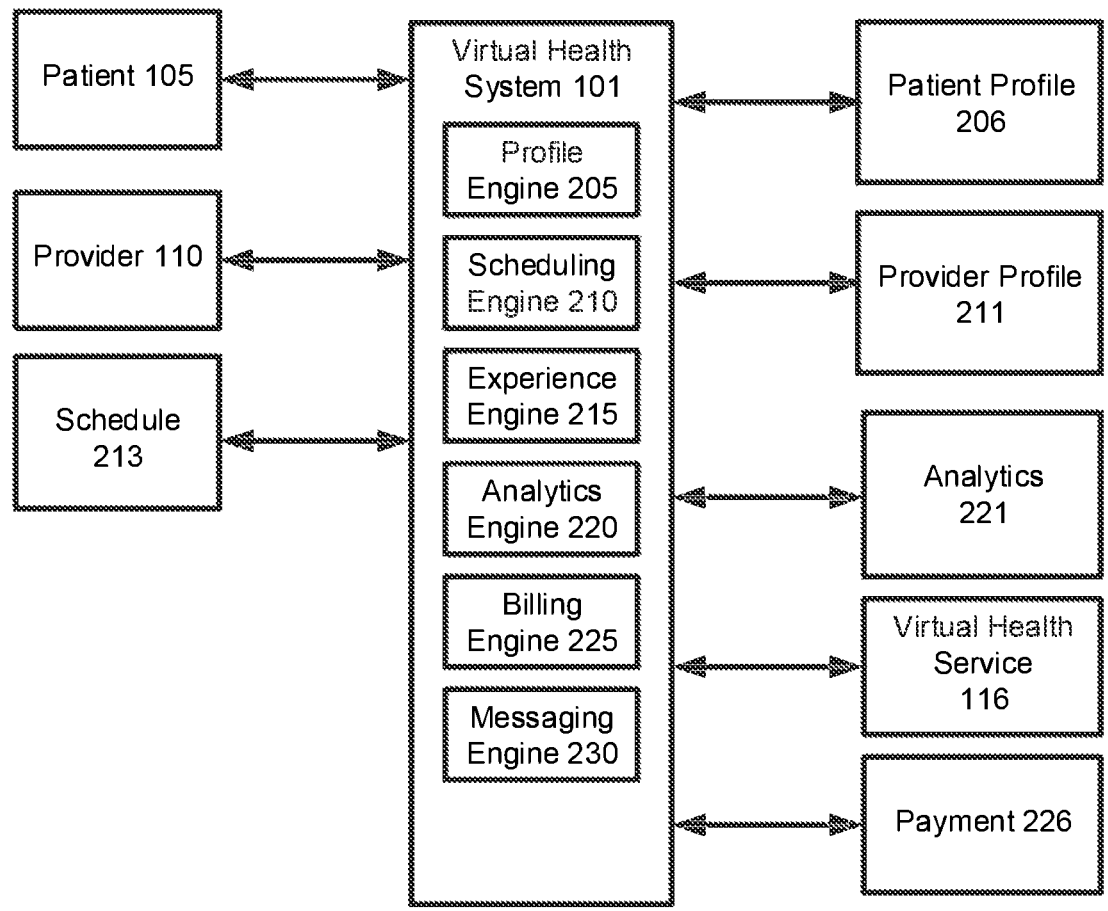
FIG. 2 is an illustration of an example virtual health system.

As described further with respect to FIG. 2, the virtual health system 101 provides functionality to facilitate the scheduling and delivery of virtual health services 116. In particular, the virtual health system 101 allows providers 110 to create profiles, set their desired compensation, and provide their available schedules for delivering virtual health services 116. The virtual health system 101 allows patients 105 to search for providers 110 who meet their health criteria and set appointments with available providers 110. The virtual health system 101 connects the patients 105 with the providers 110 using a selected or preferred communications means (e.g., video conference or telephone) to provide the selected virtual health services 116. Before or after the virtual health services 116 are completed, the virtual health system 101 facilitates automatic payment for the services 226 via payment methods selected by the patients 105 (e.g., credit card or bank transfer).

Additional functionality provided by the virtual health system 101 includes advanced scheduling based on provider 110 availability. Providers 110 can provide their availability and specify requirements such as the desired length of services 116, how much break time they need between services 116, and whether they want services 116 to align or begin at a particular time. This provides additional flexibility to both the patient 105 and provider 110 when scheduling virtual health services and ensures that the providers 110 maximize their ability to provide virtual health services 116.

Another functionality provided by the virtual health system 101 is the handling and transfer of patient 105 health or medical records. The virtual health system 101 may, for each patient 105, maintain records of the virtual health services 116 provided by the providers 110 to the patient 105. The records may include any feedback, notes, diagnoses, and prescriptions provided to the associated patient 105 by the providers 110. In the event that a patient 105 would like to begin seeing a new provider 110, or has been referred to a new provider 110, the virtual health system 101 may facilitate providing the new provider 110 access to the records only after permission has been received from the patient 105 by the virtual health system 101. This may allow patients 105 to easily move between providers 110 associated with the virtual health system 101 while protecting privacy and providing HIPAA compliance.

Another functionality provided by the virtual health system 101 is the use of analytics to improve patient care. For example, the virtual health system 101 may collect and process data related to the virtual health services 116 such as service length, patient 105 and provider 110 reviews or satisfaction surveys, patient 105 assignments, appointment frequency, and patient 105 reported mental health on surveys provided by the virtual health system 101. The virtual health system 101 can use the processed data to identify virtual health service 116 features that are associated with improved patient 105 health or well-being such as appointment length, frequency, and provider 110 assignments. These features may then be recommended to the providers 110.

FIG. 2 is an illustration of an example virtual health system 101. As shown, the virtual health system 101 includes a variety of components including a profile engine 205, a scheduling engine 210, an experience engine 215, an analytics engine 220, a billing engine 225, and a messaging engine 230. More or fewer components may be supported. Some or all of the components of the virtual health system 101 may be implemented together or separately by a general purpose computing device such as the computing device 600 illustrated with respect to FIG. 6. In addition, some or all of the components may be implemented together or separately by a cloud-based computing environment.

The profile engine 205 may create, store, and manage patient profiles 206 and provider profiles 211 for one or more patients 105 and providers 110, respectively. For each patient 105, the profile engine 205 may create a patent profile 206. The patient profile 206 for a patient 105 may include information about the patient 105 such as their name, address, phone number, e-mail address, and demographics information. The patient profile 206 may include a screen name or alias that the patient 105 may like to use with respect to the virtual health system 101.

The patient profile 206 may also include medical records associated with the patient 105. Initially, the medical records may be provided by the patient 105. Over time, the medical records may be updated to include information about virtual health services 116 provided by the providers 110 to the patient 105, notes from the providers 110 about the patient 105, medications prescribed to the patient 105 by the providers 110, and any diagnoses provided by the providers 110. As may be appreciated, the medical records portion of the patient profile 206 may be kept private and may only be viewed by a provider 110 authorized by the patient 105.

When the patient 105 initially connects to the virtual health system 101, the profile engine 205 may collect the information for the patient profile 206, may help the patient 105 select an alias or username, and may help the patient 105 create a password. In addition, the profile engine 205 may assign a unique number or identifier to the patient 105. The profile engine 205 may then store the patient profile 206.

For each provider 110, the profile engine 205 may create a provider profile 211. The provider profile 211 for a provider 110 may include information about the provider 110 such as their name, address, phone number, e-mail address, and demographics information. The provider profile 211 may include a screen name or alias that the provider 110 may like to use with respect to the virtual health system 101.

In addition, the provider profile 211 may include information about the provider 110 such as their title, specialty, the colleges and universities that they attended, and a description of their healthcare practice and healthcare interests. The provider profile 211 may further include indications of awards that the provider 110 received and papers that were authored by the provider 110. The provider profile 211 may further include one or more images or photographs of the provider 211. The profile engine 205 may create a provider profile 211 for each provider 110 similarly as described above for the patient profile 206.

As may be appreciated, some or all of the information from the provider profile 211 may be visible to patients 105. In particular, the patients 105 may be able to search for providers 110 based on information from the provider profiles 211 such as medical or health specialties and/or specific health issues treated by the providers 110.

The scheduling engine 210 may create a schedule 213 for each provider 110 associated with the virtual health system 101. The schedule 213 for a provider 110 may indicate the times during which the provider 211 is available to provide virtual health services 116 to patients 105 and may indicate the times that the provider 211 has already been scheduled to provide virtual health services 116.

In some embodiments, the scheduling engine 210 may initially create the schedule 215 for a provider 110 based on information requested from the provider 110. The information may include the times and dates that the provider 110 is available to provide virtual health services 116, a minimum or maximum length of time for a virtual health service 116 (e.g., what is the shortest and longest health service that you will provide?), a minimum amount of time between virtual health services (e.g., how much break do you need between services?), service alignment (e.g., does the provider 110 prefer to begin services on the hour, half-hour, or has no preference), a maximum amount of time that the provider 110 would like to work for the virtual health system 101 during a week (e.g., twenty hours vs. forty hours), a desired cost for services 116, a minimum acceptable cancelation time (e.g., one day before, one hour before, fifteen minutes before), and a cancelation charge (e.g., flat fee or percentage of service cost).

With respect to available dates and times, in some embodiments, the scheduling engine 210 may interface with one or more calendar applications (e.g., Microsoft Outlook™) and may determine the available times based on the calendar applications. If at a later time a provider 110 adds an event to their calendar, the scheduling engine 210 may readjust the schedule 213 of the provider 110 to reflect that the time associated with the event is no longer available.

The scheduling engine 210 may further facilitate the scheduling of one or more virtual health services 116 for patients 105 based on the schedule 213 associated with each provider 110. In some embodiments, the patients 105 may select a desired provider 110 to have a virtual health service 116 and may provide a desired date range for the service 116. In response to the selection, the scheduling engine 210 may retrieve the schedule 213 associated with the selected provider 110 and may generate a list of dates and times that the provider 110 is available for virtual health services 116.

In some embodiments, the scheduling engine 210 may generate the list of available dates and times, by first determining the dates and times that the provider 110 is available for services 116 that fall within the dates and times provided by the patient 105 (i.e., which times has the provider 110 not yet been scheduled). The scheduling engine 210 may then determine, from among the dates and times, all dates and times that meet the various requirements of the providers 110. The requirements including service length, time between events, alignment, etc. The list of determined dates and times that meet the provider 110 availability requirements may be displayed to the patient 105, and the patient 105 can select from among the displayed times. If the patient 105 selects a time for a virtual health service 116, the virtual health service 116 may be added to the schedule 213 of the provider 110 and a schedule 213 for the patient 105.

In some embodiments, the scheduling engine 210 may allow patients 105 to be put on waiting lists for unavailable times for a provider 110. The scheduling engine 210 may, along with the available times, display the times when the provider 110 is unavailable. If the patient 105 selects an unavailable time, the scheduling engine 210 may offer to add the patient 105 to a waitlist for the provider 110 at the selected time. In the event that the scheduled patient 105 cancels, the scheduling engine 210 may offer the time to patients 105 from the waitlist.

In some embodiments, when a patient 105 first requests or schedules an appointment with a provider 110, the scheduling engine 210 may provide the patient 105 an intake form associated with the provider 110. The intake form may include various questions for the patient 105 such as demographic questions, and questions about the mental health of the patient 105. Once the patient 105 completes the intake form, the scheduling engine 210 may store or associate the form with the patient profile 206.

In addition, before the patient 105 schedules a virtual health service 116 with a provider 110, the scheduling engine 215 may allow the patient 105 to send some number of communications (e.g., e-mails) to the provider 110. For example, the patient 105 may have questions about the provider 110 such as their philosophy or experience with a particular mental health issue. However, to prevent the patient 105 from overwhelming the provider 110, the patient 105 may be limited to a maximum number of communications, such as three messages. More or fewer messages may be supported. When the provider 110 responds to a communication from a patient 105, the patient 105 may be credited with some number of additional communications with the provider 110.

In some embodiments, the scheduling engine 210 may also facilitate the creation of group virtual health services 116. A group virtual health service may be a health service 116 that has at least one provider 110 and two or more patients 105. A group health service 116 may further include multiple providers 110.

When a provider 110 initially creates a group virtual health service 116, the provider 110 may identify a primary provider 110 that will control or be responsible for running the group virtual health service 116 along with other providers 110 that will participate. The provider 110 may also identify a length of time for the virtual health service 116, the number of patients 105 that may participate, a cost for the group virtual health service 116, and may provide a description for the group virtual health service 116. Patients 105 may be able to search for available group virtual health services 116 similarly as described above for non-group virtual health services 116.

The experience engine 215 may facilitate the delivery of virtual health services 116 to patients 105 and providers 110. The experience engine 215 may receive the schedules 213 for each provider 110 and patient 105. At a configurable amount of time (e.g., fifteen minutes, ten minutes, five minutes, etc.) before a virtual health service 116 is scheduled to begin, the experience engine 215 may send an electronic message (e.g., email or text message) to the patient 105 and the provider 110. The message may include a link through which the patient 105 can access the virtual health service 116 (e.g., video chat). The message may further include a link or user interface element that the patient 105 and/or provider 110 can use to cancel or reschedule the virtual health service 116 if necessary.

In embodiments with a waitlist, the experience engine 215 may send an additional message to waitlist patients 105 at some time (e.g., fifteen minutes, thirty minutes, forty-five minutes, etc.) prior to the start of the virtual health service 116. The message may ask each patient 105 to confirm that they would like to attend the virtual health service 116. In the event that the scheduled patient 105 cancels or declines the virtual health service 116, a next patient 105 on the waitlist may be offered the service 116 as described above.

In some embodiments, the experience engine 215 may control and facilitate the technology that is used to provide the virtual health services 116 (e.g., video chats or telephone call). Alternatively, the experience engine 215 may use existing technologies or services provided by third-parties (e.g., FaceTime™, Zoom™, and Microsoft Teams™).

The experience engine 215 may allow the provider 110 to record notes and observations made during the virtual health service 116, as well as a transcript or recording of the virtual health service 116. The experience engine 215 may store notes and observations in the patient profile 206 as part of the medical records. The notes may include any diagnoses made by the provider 110 during the virtual health service 116. Depending on the embodiment, the patient 105 may first consent to the recording of the virtual health service 116 before the provider 110 is able to make any recordings.

The experience engine 215 may allow the provider 110 to assign assignments or "homework" to the patient 105. The assignments may include reading assignments, journaling assignments, questionnaires, and activities, for example. The experience engine 215 may provide an interface to create the assignments, may track which assignments were completed, may track how long each assignment or assignment section took to complete, and may send reminders to the patient 105 about pending assignments. Information about each assignment may be stored in the patient profile 206 as part of the medical records.

Depending on the embodiment, when the experience engine 215 determines that a patient 105 has completed an assignment, the experience engine 215 may automatically send the patient 105 an encouraging message or other communication. The message or communication may include text or other correspondence that was selected or approved by the associated provider 110, and the message or communication may appear to the patient 105 as if the message or communication had been sent by the provider 110 themselves. So that the automated nature of the message or communication is not obvious to the patient 105, the experience engine 215 may delay the delivery of the message by some configurable amount of time (e.g., 15 minutes, 30 minutes, etc.) after the patient 105 completes the assignment.

The experience engine 215 may allow the provider 110 to create and provide prescriptions for medication to the patient 105 during, or after, a virtual health service 116. The prescription may be an electronic prescription that is electronically provided to the patient 105. Depending on the embodiment, the prescription may include a link to an entity that may be used to fulfil the prescription (e.g., a mail-order pharmacy). When a prescription is filled through the virtual health system 101, the virtual health system 101 and/or the provider 110 may receive a fee or a percentage of the cost of the prescription.

The experience engine 215 may further allow the provider 110 to view the medical records associated with the patient 105. The provider 110 may view the notes and observation from previous virtual health services 116, information about any medications prescribed to the patient 105, and any prior diagnoses made for the patient 105. In addition, the provider 110 may view the assignments completed (or not completed) by the patient 105.

Depending on the embodiment, the experience engine 215 may provide social networking functionality through which patients 105 and providers 110 can "friend" each other and exchange information such as images, articles, and ideas related to healthcare and virtual health services 116. The patients 105 and providers 110 may be segregated from one another so that patients 105 can only communicate with other patients 105, and vice versa.

The experience engine 215 may periodically request that patients 105 submit reviews or evaluations of providers 110. The evaluations may ask the patients 105 to review the provider 110 on a variety of metrics and to provide an overall score for the provider 110. The patients 105 may also be asked to periodically indicate how they are feeling and whether they believe that the virtual health services 116 provided by a provider 110 have been effective.

In some embodiments, the virtual health system 101 may provide virtual health services 116 to patients 105 that are employees of a company or other entity. The experience engine 215 may periodically survey the employee patients 105 regarding their overall happiness and/or mental health and/or other characteristics, behaviors, feelings, etc. The results of the surveys may be aggregated, anonymized, and provided to the associated companies. The anonymized results may be further provided to providers 110, or other entities such as investors, for example.

The experience engine 215 may further provide awards, trophies, or other encouragements to both the patients 105 and providers 110 for participating in virtual health services 116. For example, patients 105 may be provided with "trophies" for attending their first virtual health service 116, meeting certain milestones (e.g., attend five, ten, or one hundred services 116), or completing their assignments for some number of consecutive weeks. These "trophies" can be added to the patient profiles 206 and displayed in messages sent by the patients 105.

Providers 110 may similarly be provided with "trophies" for having provided some number of virtual health services 116, for receiving a high score or rating from patients 105, or for performing some number of services 116 in one day or one week. These "trophies" and average scores or ratings can be displayed in the provider profile 211 and may be considered by patients 105 when selecting providers 110.

In some embodiments, the experience engine 215 may further provide patients 105 with credits for participating in virtual health services 116 or for completing assignments. These credits may be redeemed by the patients 105 for free or discounted virtual health services 116, for merchandise, or for goods or services provided by affiliated companies or entities.

The experience engine 215 may protect the privacy of the medical records associated with each patient 105. When a patient 105 first schedules a virtual health service 116 with a provider 110, the experience engine 215 may provide an electronic message that asks the patient 105 to consent to having the particular provider 110 view the patient's 105 medical records. Only after the patient 105 consents is the particular provider 110 allowed access to the medical records.

The experience engine 215 may further allow patients 105 to consent to other providers 110 viewing their medical records. For example, a first provider 110 may be currently seeing a patient 105 virtually but would like to refer the patient 105 to a second provider 110 associated with the virtual health system 101. The first provider 110 may make the referral by searching for the second provider 110 and providing a message to the second provider 110. If the second provider 110 accepts the referral, the patient 105 may be automatically provided an electronic message asking the patient 105 to consent to the second provider 110 viewing their health and medical records. Note that the patient 105 may withdraw consent from any provider 110 at any time through the experience engine 215.

After a virtual health service 116 ends, the provider 110 and patient 105 may agree to one or more follow-up services 116 or may agree to make the service 116 a recurring service 116. The experience engine 215 may facilitate the creation of the follow-up services 116 through the scheduling engine 210.

The analytics engine 220 may collect and process data about the virtual health services 116 and may generate one or more analytics 221 that may be used to improve outcomes related to the virtual health services 116. In particular, the analytics engine 220 may track interactions of the patients 105 and providers 110 made through the virtual health system 101 and may provide feedback related to the tracked interactions in the form of analytics 221.

One example of analytics 221 that may be provided by the analytics engine 220 is feedback related to the assignments provided by the providers 110 to their patients 105 through the virtual health system 101. As noted above, information about the assignments such as whether they were completed, how long they took to complete, and how long each question took to complete may be tracked by the experience engine 215. The analytics engine 220 may process the tracked data to provide feedback in the form of analytics 221 to the providers 110.

For example, with respect to an assignment, the analytics 221 may show the average amount of time patients 105 spent responding to each question, and the overall completion rate for the assignment by patients 105. The provider 110 may then determine which questions are not being answered by patients 105 or that are taking up too much time.

The analytics engine 220 may present the analytics 221 for the assignment along with analytics 221 collected for assignments created by other providers 110. The provider 110 can then see how their assignments compare with the assignments of other providers 110 in terms of completion rates.

As another example, the analytics engine 220 may collect data related to the intake forms completed by patients 105 after making an appointment with a provider 110. As described above, when a patient 105 books a first appointment with a provider 110, the virtual health system 101 may automatically provide the patient 105 with an intake form that is created and/or provided by the provider 110. Similar to the assignments, data about the intake forms may be collected for each provider 110 including time spent on each question in the form, the completion rate for each question, and the overall completion rate or abandonment rate (i.e., how many patients 105 actually submit or do not submit the completed intake form).

The analytics engine 220 may use the data about the intake forms to provide analytics 221 about the intake forms to each provider 110. The analytics 221 provided to a provider 110 may include the average amount of time that the patients 105 spent completing the form along with the average amount of time spent on intake forms associated with the other providers 110. The provider 110 may then determine to adjust their intake forms based on the analytics 221.

The billing engine 225 may facilitate providing payments 226 to providers 110 for virtual health services 116. Once a virtual health service 116 begins, the billing engine 225 may put a hold on the credit card associated with the patient 105 (or patients 105) associated with the service 116. The billing engine 225 may determine the credit card from the patient profile 206 associated with the patient 105 and may determine a cost for the service 116 based on information associated with the provider profile 211 or otherwise provided by the provider 110. Note that depending on the embodiment, some providers 110 may offer one or more free virtual health services 116.

After the virtual service 116 has begun, the billing engine 225 may charge the credit card of the patient 105 for the cost of the service 116. The billing engine 225 may then deposit an amount of money into an account associated with the provider 110 minus a fee charged by the virtual health system 101 to the providers 110. The fee may be a flat fee or may be a percentage of the cost of the virtual health services 116. Depending on the embodiment, the fee may be constant, or may decrease based on the total number of virtual health services 116 provided by the provider 110 in a given period (e.g., week, month, quarter, or year). For example, the provider 110 may pay a 20% fee for the first fifty services 116 conducted in a year, and a 15% fee for all services 116 provided thereafter. The fee may remain at a reduced rate so long as the provider 110 continues to provide virtual health services 116 at a specified frequency. Depending on the embodiment, the billing engine 225 may determine that a virtual health service 116 has begun when both the patient 105 and the provider 110 have connected to or initiated the virtual health service 116.

The billing engine 225 may further reduce or adjust the fee to encourage providers 110 to provide services at certain dates or times. For example, the billing engine 225 may lower the fee for virtual health services 116 that occur between 9 pm and 6 am or may lower the fee for virtual health services 116 that occur on certain holidays.

The billing engine 225 may further provide payments 226 to providers 110 when a patient 105 cancels outside of a cancelation window. The window may be a default window or may be specified by the provider 110 in their provider profile 211. The amount of the cancellation fee may further be a default fee or may be specified by the provider 110.

The billing engine 225 may allow for payment to providers 110 via one or more insurance companies or third-party payors (e.g., government payors). The billing engine 225 may use insurance information associated with each patient 105 to determine the insurance company to charge and a co-pay that may be required from the patient 105. Depending on the embodiment, if the insurance company will not pay the full amount charged by the provider 110, the billing engine 225 may collect any remaining payment 226 due from the patient 105 as described above.

The messaging engine 230 may facilitate communication channels (e.g., chat or messaging applications) that may be used by patients 105 and providers 110 to communicate with each other through the virtual health system 101. The messaging engine 230 may allow patients 105 to initiate communication by searching for and selecting among a customized list of providers 110 based on a number of criteria (geographic location, specialty, insurance affiliation, etc.). In some embodiments, before the messaging engine 230 allows the patient 105 and the provider 110 to communicate, the provider 110 may first agree or consent to continue the communication.

The messaging engine 230 may allow for the sending, transferring, and saving of a variety of documents between patients 105 and providers 110, or providers 110 and other providers 110. These documents may include a variety of documents that may be used to provide medical or health services to patients 105 including, but not limited to, healthcare referrals, patient medical records and notes, insurance documentation, radiologic images or reports, and procedure records. Other documents may be supported.

In some embodiments, the messaging engine 230 may allow providers 110 to share information about patients 105 while maintaining strict HIPAA compliance. For example, a first provider 110 may be discussing a patient 105 with a second provider 110 in a chat application. The first provider 110 may be currently treating the patient 105 and would like to share medical records associated with the patient 105 with the second provider 110. Accordingly, the first provider 110 may drag and drop or attach the records into the chat application.

In response, the messaging engine 230 may first determine whether the patient 105 has consented for the second provider 110 to view their medical records, and if not, the messaging engine 230 may send a message or communication to the patient 105 asking for consent to the sharing of their medical records with the second provider 110. If the patient 105 consents, then the messaging engine 230 may allow the second provider 110 to view the patient records in the chat application.

In some embodiments, the messaging engine 230 may initially restrict or provide for minimal communication between providers 110 and patients 105 to both protect the privacy of the patients 105 and providers 110 as well as prevent the solicitation of patients 105 by providers 110. For example, when a first provider 110 attempts to communicate or start a chat session with a second provider 110, the messaging engine 230 may first ask the second provider 110 to consent to the communication.

With respect to communications between providers 110 and patients 105, when a provider 110 with no current or previous clinical relationship with a patient 105 attempts to communicate with the patient 105, the messaging engine 230 may prevent the provider 110 from sending the communication. This may prevent providers 110 from spamming patients 105 with unsolicited requests to attend virtual health services 116.

The messaging engine 230 may further allow chats, and other communications that relate to a patient 105 to be stored or linked to the medical history or records associated with the patient 105. When a provider 110 is discussing a patient 105 with either the patient 105 themselves or another authorized provider 110, the messaging engine 230 may allow the provider 110 to associate some or all of the communication with the medical records of the patient 105. For example, the messaging engine 230 may allow the provider 110 to highlight portions of a chat and to associate the highlighted portions with the medical records of the patient 105. Depending on the embodiment, the portions of the chat that are about the patient 105 may be automatically identified and highlighted by the messaging engine 230 using natural language processing, or may be manually highlighted by the provider 110.

In some embodiments, the messaging engine 230, rather than save the chat or portions of the chat with the medical records of a patient 105, may allow providers 110 to create bookmarks or links to the portions of the chat that are related to the patient 105. The bookmarks or links may then be stored with the medical records of the patient 105 or shared with other providers 110. The bookmarks may then be later used to retrieve the associated chat or chat portions when selected.

Where providers 110 are discussing multiple patients 105 in a single chat, the messaging engine 230 may create multiple bookmarks that each reference a portion of the chat that corresponds to a different patient 105. The bookmarks may be stored along with the medical records of their associated patient 105. At a later time when a bookmark is used to retrieve the chat, the messaging engine 230 may only allow the portions of the chat that are associated with the patient 105 corresponding to the bookmark to be viewed.

In some embodiments, the messaging engine 230 may allow providers 110 to transfer patient 105 specific conversation from a general conversation with other providers 110 to a patient 105 specific conversation that may be linked to the medical records associated with a patient 105. For example, a first provider 110 may be having a chat discussion with a second provider 110 about a variety of topics. At some point in the conversation, a particular patient 105 may be discussed by the first and second providers 110. After they are finished discussing the patient 105, the first (or second) provider 110 may select or highlight the parts of the chat that are about the particular patient 105 and may indicate to the messaging engine 230 that these parts of the chat should be associated with the patient 105. The messaging engine 230 may then generate a new chat that includes just the highlighted messages and may associate or bookmark the new chat with the medical records of the patient 105 as described above.

Figure 3:
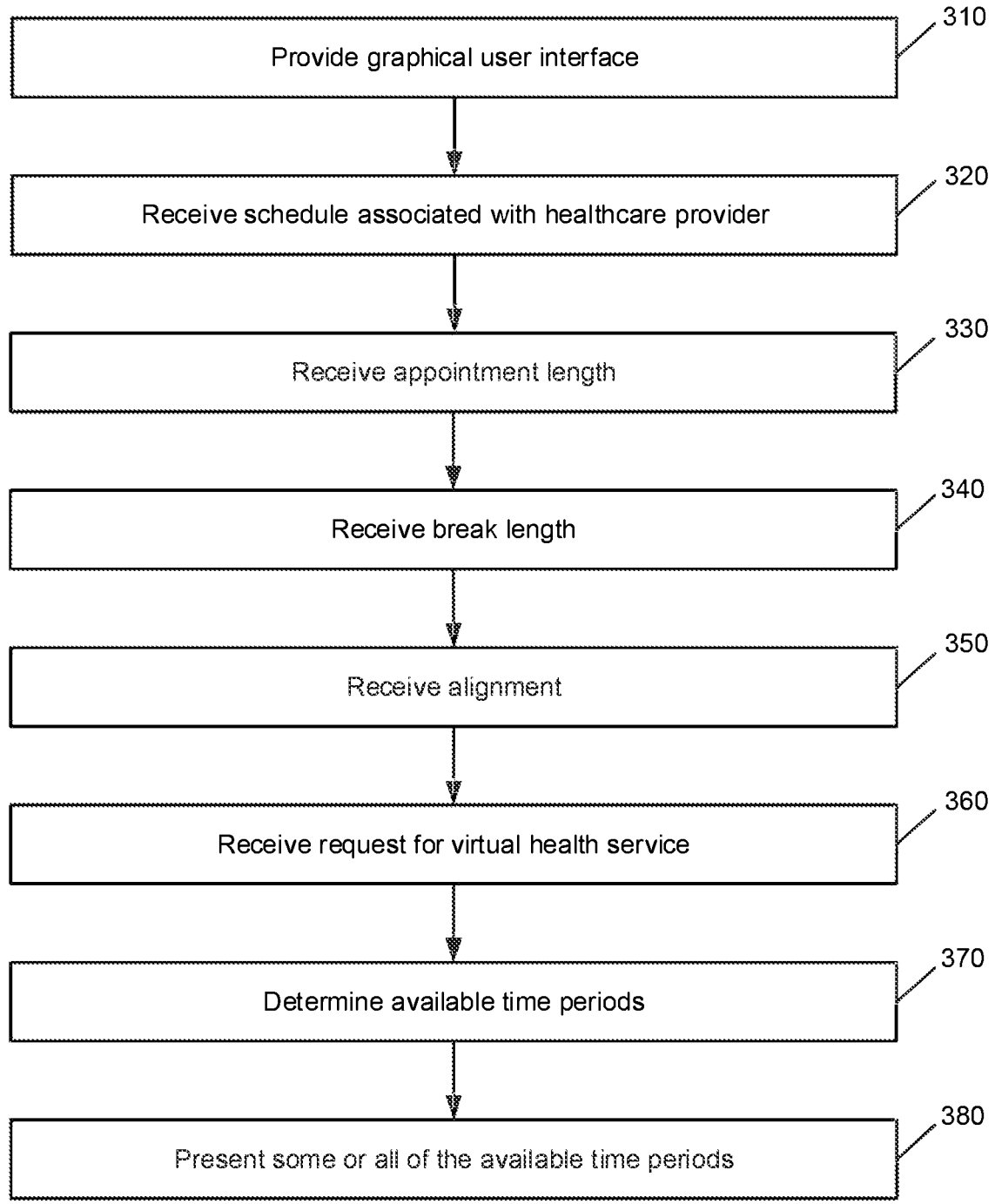
FIG. 3 is an operational flow of an implementation of a method for scheduling a virtual health service.

FIG. 3 is an illustration of a method 300 for scheduling a virtual health service 116. The method 300 may be implemented by the virtual health system 101.

At 310, a graphical user interface is provided. The graphical user interface may be provided by the virtual health system 101 to one or more patients 105 and providers 110. Depending on the embodiment, the graphical user interface may be provided by a webpage provided by the virtual health system 101 or through an "app" or application provided by the virtual health system 101. The patient 105 and providers 110 may download the app to their associated smartphones or computing devices. The patients 105 and providers 110 may use the graphical user interface to interact with the virtual health system 101 and to provide or receive virtual health services 116.

At 320, a schedule associated with a healthcare provider is received. The schedule 213 may be received by the scheduling engine 210 from the provider 110 through the graphical user interface. The schedule 213 may indicate the availability of the healthcare provider 110 to provide virtual healthcare services 116 to one or more patients 105 over a first duration of time (e.g., day, week, or month).

At 330, an appointment length is received. The appointment length may be received by the scheduling engine 210 from the provider 110 through the graphical user interface. The appointment length may indicate the range of lengths that the provider 110 desires for virtual health services 116. For example, some providers 110 may require that virtual health services 116 be at least fifty minutes in length, other providers 110 may allow shorter virtual health services 116.

At 340, a break length is received. The break length may be received by the scheduling engine 210 from the provider 110 through the graphical user interface. The break length may indicate the minimum amount of time that the provider 110 requires between virtual health services 116.

At 350, an alignment is received. The alignment may be received by the scheduling engine 210 from the provider 110 through the graphical user interface. The alignment may indicate whether the provider 110 requires that virtual health services 116 begin at any particular time. For example, some providers 110 may require that all services 116 begin on the hour, while other providers 110 may allow services 116 to begin on the hour or the half-hour.

At 360, a request for a virtual healthcare service is received. The request may be received by the scheduling engine 210 from a patient 105 through the graphical user interface. The request may identify the provider 110 and may include a second duration of time. For example, the request may include a range of dates and times that the patient is available to attend a virtual health service 116 with the provider 110.

At 370, in response to the request, available time periods are determined. The available time periods may be determined by the scheduling engine 210. The time periods may be within the first duration and the second duration and may meet all of the requirements and preferences provided by the provider 110 (i.e., the appointment length, break length, and alignment).

At 380, some or all of the determined time periods are presented. The determined periods may be presented by the scheduling engine 210 to the patient 105 through the graphical user interface. The patient 105 may then select one of the time periods, and a virtual health service 116 may be scheduled with the provider 110. Depending on the embodiment, a hold may be placed on a credit card or other payment means associated with the patient 105 for the cost of the virtual health service 116.

Figure 4:
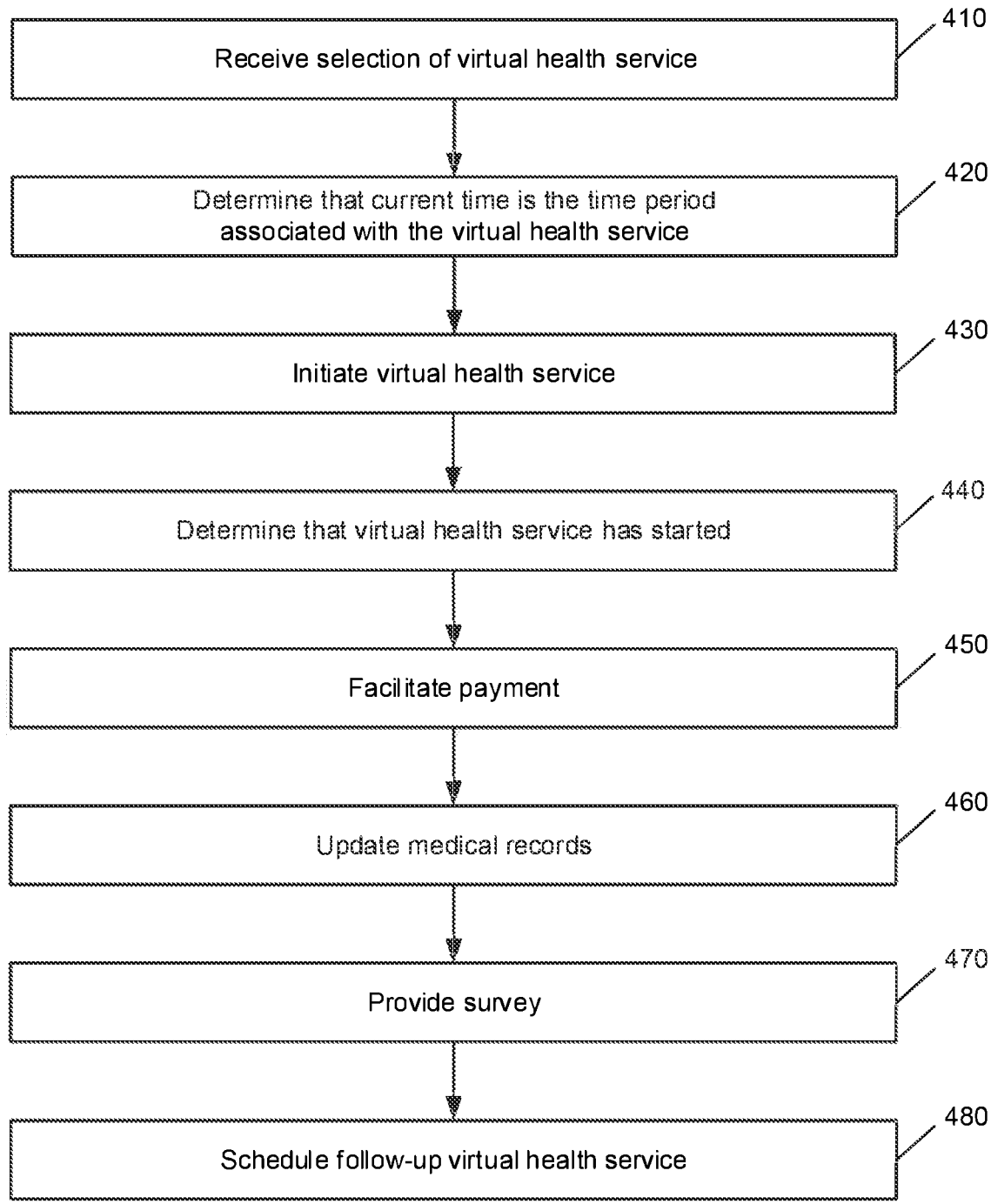
FIG. 4 is an operational flow of an implementation of a method for conducting a virtual health service.

FIG. 4 is an illustration of a method 400 for conducting a virtual health service 116. The method 400 may be implemented by the virtual health system 101.

At 410, a selection of a virtual health service is received. The selection may be received by the scheduling engine 210. The virtual health service 116 may be associated with a time period in the future. The virtual health service 116 may be a video chat or communication with a healthcare provider 110.

At 420, that a current time is a starting time of the virtual health service is determined. The determination may be made by the experience engine 215. Depending on the embodiment, the experience engine 215 may determine that the current time is within some threshold of the start time (e.g., five minutes, ten minutes, etc.).

At 430, in response to the determination, the virtual health service is initiated. The virtual health service 116 may be initiated by the experience engine 215. For example, the experience engine 215 may send an electronic message to the patient 105 and the provider 110 associated with the virtual health service 116. The message may include a link to start or otherwise cause the virtual health service 116 to begin.

At 440, that the virtual health service has started is determined. The experience engine 215 may determine that the virtual health service 116 has started when both the provider 110 and the patient 105 have accessed or signed on to the virtual health service 116.

At 450, payment for the virtual health service is facilitated. The payment 226 may be facilitated by the billing engine 225. In some embodiments, the billing engine 225 may facilitate payment by debiting a credit card associated with the patient 105 and crediting an account associated with the healthcare provider 110. In addition, the billing engine 225 may reduce the payment 226 to the provider 110 by a fee that is paid to the virtual health system 101. In some embodiments, the billing engine 225 may facilitate payment 226 through one or more insurance providers or third-party payors associated with the patient 105.

At 460, medical records associated with the patient are updated. The medical records may be updated by the experience engine 215. The medical records may be updated to reflect that the virtual health service 116 was provided, to include any notes or observations made by the provider 110 during or after the service 116, and any prescriptions that were provided to the patient 105. Other information may be included in the medical records.

At 470, a survey is provided. A survey may be provided by the experience engine 215 after the virtual health service 116 has ended. The survey may include questions for the patient 110 about the service 116 and the provider 110. The survey may ask the patient 105 to rate the service 116 and provider 110 on a variety of metrics. The survey may also ask the patient 110 questions about their overall mental well-being. The answers to the survey may be used by the analytics engine 220 to identify virtual health service 116 best practices that lead to improved patient 105 well-being and virtual health service 116 satisfaction.

At 480, a follow-up virtual health service is scheduled. The follow-up service may be scheduled automatically by the scheduling engine 210 after the virtual health service 116 has ended.

Figure 5:
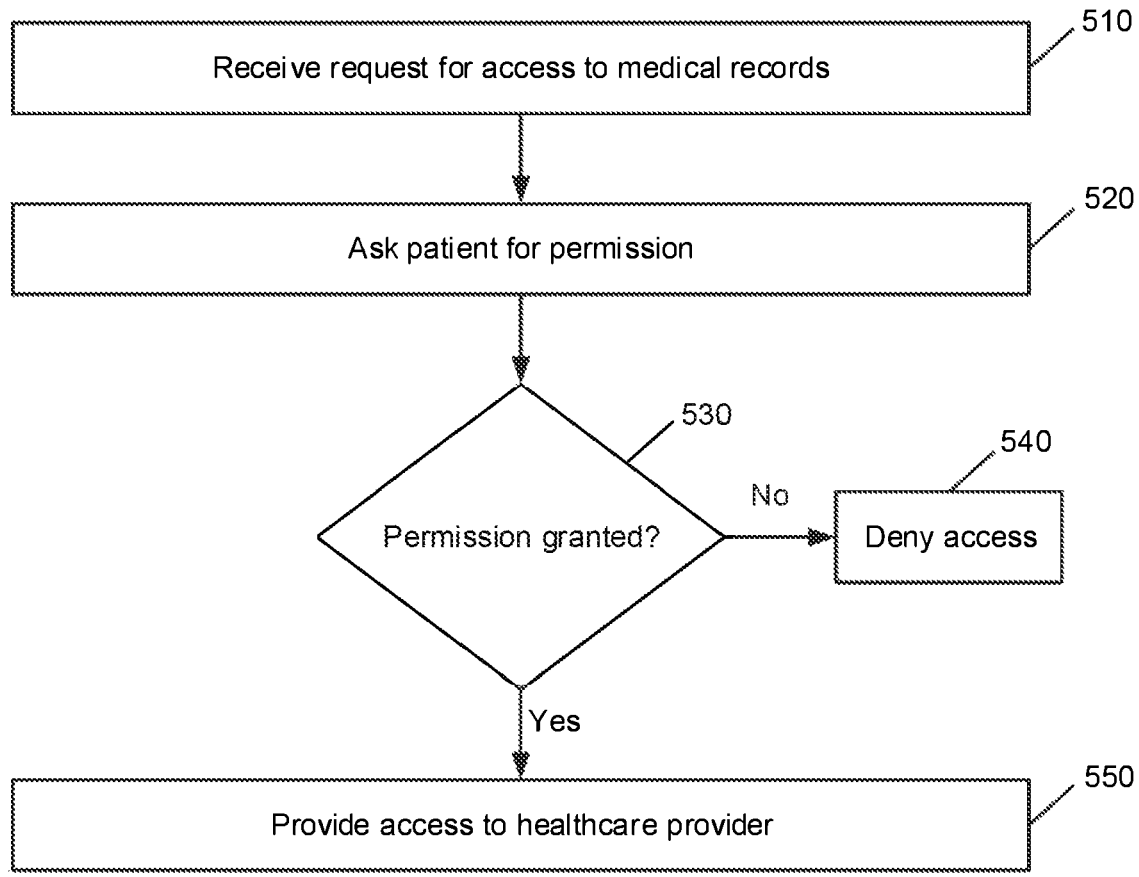
FIG. 5 is an operational flow of an implementation of a method for providing access to medical records in a virtual health system.

FIG. 5 is an illustration of a method 500 for providing access to medical records in a virtual health system 101. The method 500 may be implemented by the virtual health system 101.

At 510, a request for access to medical records is received. The request may be received by the profile engine 205 from a provider 110. For example, a provider 110 may have received a referral to treat a patient 105 associated with the medical records or may be collaborating with another provider 110 who treats the patient 110. Depending on the embodiment, the provider 110 may provide the request using a graphical user interface and/or messaging system provided by the virtual health system 101. The medical records may be part of the patient profile 206 associated with the patient 105 and may only be viewed or accessed by providers 110 with permission from the associated patient 105.

At 520, the patient is asked for permission. The patient 105 may be asked for permission by the profile engine 205. Depending on the embodiment, the profile engine 205 may send an electronic message to the patient 105 that identifies the provider 110 requesting access to their medical records. The message may include a link or user interface element that the patient 105 may use to approve or deny the request and to request additional information about the provider 110.

At 530, it is determined whether the patient 105 has granted permission to view their medical records. If so, the method 500 may continue at 550. Otherwise, the method 500 may continue at 540.

At 540, access to the medical records of the patient is denied. The access may be denied by the profile engine 205.

At 550, access to the medical records of the patient is provided. The access may be provided by the profile engine 205. Depending on the embodiment, the profile engine 205 may provide an electronic message to the provider 110. The message may include a link to the medical history associated with the patient.

Figure 6:
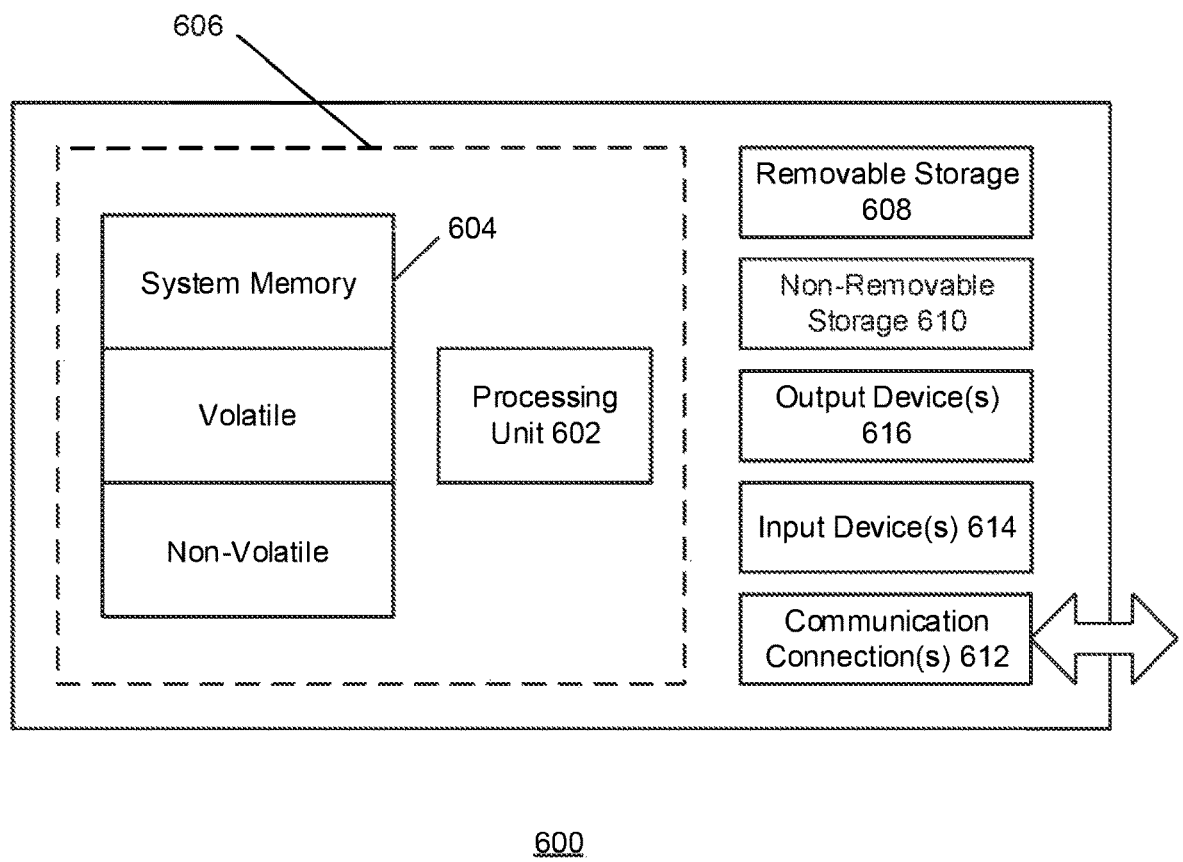
FIG. 6 shows an exemplary computing environment in which example embodiments and aspects may be implemented.

FIG. 6 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 6, an exemplary system for implementing aspects described herein includes a computing device, such as computing device 600. In its most basic configuration, computing device 600 typically includes at least one processing unit 602 and memory 604. Depending on the exact configuration and type of computing device, memory 604 may be volatile (such as random access memory (RAM)), non-volatile (such as read-only memory (ROM), flash memory, etc.), or some combination of the two. This most basic configuration is illustrated in FIG. 6 by dashed line 606.

Computing device 600 may have additional features/functionality. For example, computing device 600 may include additional storage (removable and/or non-removable) including, but not limited to, magnetic or optical disks or tape. Such additional storage is illustrated in FIG. 6 by removable storage 608 and non-removable storage 610.

Computing device 600 typically includes a variety of computer readable media. Computer readable media can be any available media that can be accessed by the device 600 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 604, removable storage 608, and non-removable storage 610 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 600. Any such computer storage media may be part of computing device 600.

Computing device 600 may contain communication connection(s) 612 that allow the device to communicate with other devices. Computing device 600 may also have input device(s) 614 such as a keyboard, mouse, pen, voice input device, touch input device, etc. Output device(s) 616 such as a display, speakers, printer, etc. may also be included. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

As used herein, the singular form "a," "an," and "the" include plural references unless the context clearly dictates otherwise. As used herein, the terms "can," "may," "optionally," "can optionally," and "may optionally" are used interchangeably and are meant to include cases in which the condition occurs as well as cases in which the condition does not occur.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for providing virtual healthcare services comprising:
    requesting permission from a patient to allow a first healthcare provider access to medical records associated with the patient;
    receiving permission from the patient to allow the first healthcare provider access to the medical records;
    in response to receiving the permission, providing the first healthcare provider access to the medical records;
    facilitating communication between the first healthcare provider and a second healthcare provider through a communication medium;
    detecting that the first healthcare provider has attached the medical records into the communication medium;
    in response to detecting that the first healthcare provider has attached the medical records into the communication medium, requesting permission from the patient to allow the second healthcare provider access to the medical records pursuant to a referral from the first healthcare provider by automatically generating and sending an electronic message to the patient, wherein the electronic message includes a user interface element that the patient entity may use to approve or deny the request;
    receiving permission from the patient to allow the second healthcare provider access to the medical records through the user interface element; and
    in response to receiving the permission, providing the second healthcare provider access to the medical records by providing a link to the medical records in the communication medium.

2. The method of claim 1, further comprising receiving a request from the first healthcare provider to access the medical records.

3. The method of claim 1, further comprising receiving the referral for the patient to the second healthcare provider from the first healthcare provider.

4. The method of claim 1, wherein detecting that the first healthcare provider has attached the medical records into the communication medium comprises detecting that the first healthcare provider has dragged and dropped the medical records into the communication medium.

5. The method of claim 1, wherein the communication medium is a chat application.

6. The method of claim 1, wherein the first healthcare provider is a mental healthcare provider.

7. The method of claim 1, further comprising receiving and displaying messages between the first healthcare provider and the second healthcare provider by a graphical user interface.

8. The method of claim 7, further comprising:
    receiving a selection of a subset of the displayed messages, wherein the displayed messages in the subset pertain to the patient; and
    associating the subset of the displayed messages with the medical records associated with the patient.

9. The method of claim 7, further comprising:
    determining that at least one of the messages is related to the patient; and
    in response to the determination, associating the at least one of the messages with electronic medical records associated with the patient.

10. A system for providing virtual healthcare services comprising:
    at least one computing device; and
    a memory storing instructions that when executed by the at least one computing device cause the at least one computing device to:
    request permission from a patient to allow a first healthcare provider access to medical records associated with the patient;
    receive permission from the patient to allow the first healthcare provider access to the medical records;
    in response to receiving the permission, provide the first healthcare provider access to the medical records;
    facilitate communication between the first healthcare provider and a second healthcare provider through a communication medium;
    detect that the first healthcare provider has attached the medical records into the communication medium;
    in response to detecting that the first healthcare provider has attached the medical records into the communication medium, request permission from the patient to allow the second healthcare provider access to the medical records pursuant to a referral from the first healthcare provider by automatically generating and sending an electronic message to the patient, wherein the electronic message includes a user interface element that the patient entity may use to approve or deny the request;
    receive permission from the patient to allow the second healthcare provider access to the medical records through the user interface element; and
    in response to receiving the permission, provide the second healthcare provider access to the medical records by providing a link to the medical records in the communication medium.

11. The system of claim 10, further comprising instructions that when executed by the at least one computing device cause the at least one computing device to receive a request from the first healthcare provider to access the medical records.

12. The system of claim 10, further comprising instructions that when executed by the at least one computing device cause the at least one computing device to receive the referral for the patient to the second healthcare provider from the first healthcare provider.

13. The system of claim 10, further comprising instructions that when executed by the at least one computing device cause the at least one computing device to:
- receive and display messages between the first healthcare provider and the second healthcare provider by a graphical user interface;
- receive a selection of a subset of the displayed messages, wherein the displayed messages in the subset pertain to the patient; and
- associate the subset of the displayed messages with the medical records associated with the patient.

14. The system of claim 10, further comprising instructions that when executed by the at least one computing device cause the at least one computing device to:
- receive and display messages between the first healthcare provider and the second healthcare provider by a graphical user interface;
- determine that at least one of the messages is related to the patient; and
- in response to the determination, associate the at least one of the messages with electronic medical records associated with the patient.

15. A non-transitory computer-readable medium with computer-executable instructions stored thereon that when executed by a computing device cause the computing device to:
- request permission from a patient to allow a first healthcare provider access to medical records associated with the patient;
- receive permission from the patient to allow the first healthcare provider access to the medical records;
- in response to receiving the permission, provide the first healthcare provider access to the medical records;
- facilitate communication between the first healthcare provider and a second healthcare provider through a communication medium;
- detect that the first healthcare provider has attached the medical records into the communication medium;
- in response to detecting that the first healthcare provider has attached the medical records into the communication medium, request permission from the patient to allow the second healthcare provider access to the medical records pursuant to a referral from the first healthcare provide by automatically generating and sending an electronic message to the patient, wherein the electronic message includes a user interface element that the patient entity may use to approve or deny the request;
- receive permission from the patient to allow the second healthcare provider access to the medical records through the user interface element; and
- in response to receiving the permission, provide the second healthcare provider access to the medical records by providing a link to the medical records in the communication medium.

16. The non-transitory computer-readable medium of claim 15, further comprising computer-executable instructions stored thereon that when executed by the computing device cause the computing device to:
- receive and display messages between the first healthcare provider and the second healthcare provider by a graphical user interface;
- receive a selection of a subset of the displayed messages, wherein the displayed messages in the subset pertain to the patient; and
- associate the subset of the displayed messages with the medical records associated with the patient.

\* \* \* \* \*

UNITED STATES PATENT AND TRADEMARK OFFICE
CERTIFICATE OF CORRECTION

Page 1 of 1

PATENT NO. : 12,106,854 B2
APPLICATION NO. : 17/839825
DATED : October 1, 2024
INVENTOR(S) : Christian Acharte et al.

It is certified that error appears in the above-identified patent and that said Letters Patent is hereby corrected as shown below:

On the Title Page

Item (72), add as co-inventor:
-- Yipeng Peng, Philadelphia, PA (US) --

Signed and Sealed this
Fourth Day of February, 2025

Coke Morgan Stewart
*Acting Director of the United States Patent and Trademark Office*